United States Patent
Mahabob

(10) Patent No.: US 11,833,230 B1
(45) Date of Patent: Dec. 5, 2023

(54) **ROOT CANAL IRRIGANT FROM *ROSA DAMASCENA* MILL**

(71) Applicant: KING FAISAL UNIVERSITY, Al-Ahsa (SA)

(72) Inventor: Nazargi Mahabob, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/244,722

(22) Filed: Sep. 11, 2023

Related U.S. Application Data

(62) Division of application No. 18/133,020, filed on Apr. 11, 2023.

(51) Int. Cl.
*A61K 6/52* (2020.01)
*A61C 17/02* (2006.01)
*A61K 6/69* (2020.01)
*A61Q 11/00* (2006.01)

(52) U.S. Cl.
CPC ............ *A61K 6/52* (2020.01); *A61C 17/02* (2013.01); *A61K 6/69* (2020.01); *A61Q 11/00* (2013.01)

(58) Field of Classification Search
CPC . A61K 6/52; A61K 6/69; A61C 17/02; A61Q 11/00
See application file for complete search history.

(56) References Cited

U.S. PATENT DOCUMENTS

| 2007/0065394 A1 | 3/2007 | Pinney |
| 2017/0119032 A1 | 5/2017 | Patron et al. |
| 2017/0143022 A1 | 5/2017 | Wicker et al. |

OTHER PUBLICATIONS

Mahabob et al., "Preparation of Mouthwash and Gel from Rosa damascena Mill and Evaluating Its Effectiveness—An In Vivo Analysis", J Pharm Bioallied Sci. May 2019; 11(Suppl 2): S198-S202.

Karladani et al., "Investigation of the Antifungal Effect of Rosa Damascena Essential Oil and Mixed Mouthwash (Grape Vinegar and Rosa Damascena essential oil) Against Candida albicans, Candida dubliniensis, Candida parapsilosis and Candida glabrata", Avicenna J Clin Med 2019, 26(3): 151-157.

*Primary Examiner* — Trevor Love
(74) *Attorney, Agent, or Firm* — Nath, Goldberg & Meyer; Richard C. Litman

(57) ABSTRACT

A root canal irrigant, and particularly to a root canal irrigant comprising *Rosa damascena* Mill.

4 Claims, No Drawings

ROOT CANAL IRRIGANT FROM *ROSA DAMASCENA* MILL

CROSS-REFERENCE TO RELATED APPLICATION

This application is a divisional of U.S. patent application Ser. No. 18/133,020, filed on Apr. 11, 2023.

BACKGROUND

Field

The disclosure of the present patent application relates to a root canal irrigant, and particularly to a root canal irrigant comprising *Rosa damascena* Mill.

Description of the Prior Art

In dentistry, for endodontic treatment, several types of root canals are being performed, either separately or in combination. However, these root canals have various limitations and certain potential toxic side effects.

The irrigants that are currently used during the cleaning and shaping steps of the root canal can be divided into antibacterial and decalcifying agents or their combination. They include sodium hypochlorite (NaOCl), chlorhexidine, ethylene diamine tetra acetic acid (EDTA), and a mixture of tetracycline, an acid and a detergent (MTAD). Unfortunately, each of these root canal irrigants exhibit side effects on the patients to which they are administered.

To reduce the adverse effects of the synthetically derived drugs, pharma companies started exploring replacing them with herbs. Since ancient times herbs have been used for their medicinal properties in various forms. They are easily available, cost-effective and have their proven medicinal validity. In dentistry several derivatives of herbs are used in the form of mouthwash, gel, and tooth paste. However, it has proven difficult to obtain formulations using such herbs that are stable and effective to serve as an irrigant that can be used in conjunction with a root canal.

Thus, a root canal irrigant solving the aforementioned problems is desired.

SUMMARY OF THE INVENTION

*Rosa damascena* Mill is one among the 200 species of the Rosaceae family of thorny shrub plants. It is commonly known as garland rose. It is a shrub with 1-2 m in height from the Rosaceae family. Flowers of this plant are colorful, shiny, and large. Because of its fragrance and beautiful flowers, it is widely cultivated all over the world. In addition to these qualities, it is also being used for its medical properties. For example, this plant has certain anti-microbial, anti-inflammatory, and analgesic properties. However, a stable, ready to use composition containing the *Rosa damascena* Mill, perhaps in the form of a rose oil, useful for application during endodontic procedures has not yet been successfully achieved.

Accordingly, in one embodiment, the present subject matter relates to a root canal irrigant composition, comprising: 2% by weight of rose oil; 2% by weight of a nonionic surfactant comprising a mixture of linear secondary alcohols reacted with ethylene oxide; and 96% by weight of water.

In another embodiment, the present subject matter relates to a method of irrigating a mouth of a patient, the method comprising applying the root canal irrigant composition as described herein to the mouth of a patient in need thereof.

In a further embodiment, the present subject matter relates to a root canal irrigant composition, consisting of: 2% by weight of rose oil; 2% by weight of polyoxyethylene-9-nonylphenol; and 96% by weight of water.

These and other features of the present subject matter will become readily apparent upon further review of the following specification.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of nays without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine or pigs, horses, camels, poultry, rabbits, goats, dogs, cats, and the like.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In one embodiment, the present subject matter relates to a rootanal irrigant composition, comprising: 2% by weight of rose oil; 2% by weight of a nonionic surfactant comprising a mixture of linear secondary alcohols reacted with ethylene oxide; and 96% by weight of water.

In an embodiment, the nonionic surfactant used in the present root canal irrigant compositions is polyoxyethylene-9-nortylphenol, sold under the tradename Tergitol-N9.

In another embodiment, the rose oil used in the present root canal irrigant compositions is obtained from *Rosa damascena* Mill, In this regard, commercially available rose oil can be used, which oil, according to the manufacturer, was derived from dried petals of the flower by a steam distillation method. In this regard, the rose oil used can be a rose oil extract primarily made up of *Rosa damascena* Mill.

In a further embodiment, the present compositions can be made by mixing the rose oil, Tergitol-N9, and water at room temperature and proper and constant speed until a homogenous mixture is formed.

In another embodiment, the present subject matter relates to a method of irrigating a mouth of a patient, the method comprising applying a root canal irrigant composition as described herein to the mouth of a patient in need thereof.

In this regard, the patient receiving the root canal irrigant composition can be undergoing a root canal procedure when the root canal irrigant composition is applied to the mouth. In another embodiment, the root canal irrigant composition can be a liquid solution applied to the mouth of the patient to clean root canals during an endodontic procedure. In still another embodiment, the patient can be a human including, by way of non-limiting example, an adult human.

In an embodiment, it is expected that the rose oil, taken as a complete oil, will have no anti-inflammatory effect while the extract could significantly reduce edema, which may be due to inhibition of the mediators of acute inflammation. In addition, R. damascena contains vitamin C which has antioxidant and anti-inflammatory effects, meaning it is expected the compositions described herein will work as intended.

It is to be understood that the root canal irrigant comprising *Rosa Damascena* Mill is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of irrigating a mouth of a patient, the method comprising applying a root canal irrigant composition to the mouth of a patient in need thereof:
    wherein the root canal irrigant composition consists of:
        2% by weight of rose oil;
        2% by weight of polyoxyethylene-9-nonylphenol; and
        96% by weight of water,
    wherein the patient is undergoing a root canal procedure when the root canal irrigant composition is applied to the mouth.

2. The method of claim 1, wherein the patient is a human.

3. The method of claim 2, wherein the human is an adult human.

4. The method of claim 1, wherein the rose oil is obtained from *Rosa damascena* Mill.

* * * * *